(12) United States Patent
Merza (10) Patent No.: US 7,799,562 B2
(45) Date of Patent: Sep. 21, 2010

(54) HYBRIDOMA PRODUCING ANTIBODIES TO LAWSONIA INTRACELLULARIS

(75) Inventor: Malik Merza, Uppsala (SE)

(73) Assignee: Boehringer Ingelheim Vetmedica GmbH (DE)

( * ) Notice: Subject to any disclaimer, the term of this patent is extended or adjusted under 35 U.S.C. 154(b) by 0 days.

(21) Appl. No.: 12/606,179

(22) Filed: Oct. 26, 2009

(65) Prior Publication Data

US 2010/0112608 A1    May 6, 2010

Related U.S. Application Data (62) Division of application No. 11/875,538, filed on Oct. 19, 2007, now Pat. No. 7,635,590, which is a division of application No. 11/158,800, filed on Jun. 22, 2005, now Pat. No. 7,303,891.

(30) Foreign Application Priority Data

Jun. 24, 2004 (EP) .................................. 04014804
Nov. 16, 2004 (EP) .................................. 04027193

(51) Int. Cl.
*G01N 33/554* (2006.01)
*C07K 16/12* (2006.01)
*C12N 5/06* (2006.01)

(52) U.S. Cl. ........................................ 435/346; 435/326
(58) Field of Classification Search ....................... None
See application file for complete search history.

(56) References Cited

U.S. PATENT DOCUMENTS

| | | | |
|---|---|---|---|
| 5,130,232 A | 7/1992 | Lee et al. | |
| 5,714,375 A | 2/1998 | Knittel et al. | |
| 7,303,891 B2 | 12/2007 | Merza | |
| 7,635,590 B2 | 12/2009 | Merza | |

FOREIGN PATENT DOCUMENTS

| | | |
|---|---|---|
| EP | 1 219 711 A2 | 7/2002 |
| EP | 1 403 643 A1 | 3/2004 |
| WO | 02/26250 A2 | 4/2002 |
| WO | 2004/033631 A2 | 4/2004 |
| WO | 2005/070958 A2 | 8/2005 |

*Primary Examiner*—Robert A Zeman
(74) *Attorney, Agent, or Firm*—Michael P. Morris; Mary-Ellen M. Devlin; Joyce L. Morrison (57) ABSTRACT

The present invention relates to the field of animal health and in particular to *Lawsonia intracellularis*. In particular, the invention relates to a method of diagnosing *Lawsonia intracellularis* infection and a diagnostic test kit using *Lawsonia intracellularis*-specific antibodies. The invention also relates to the use of the method or test kit for diagnosing *Lawsonia intracellularis* infections.

1 Claim, 5 Drawing Sheets

| IFA test results | farm 1 | farm 2 | farm 3 |
|---|---|---|---|
| gilts | 0 / 0 / 9 | 3 / 1 / 6 | 0 / 6 / 4 |
| sows | 1 / 3 / 6 | 0 / 0 / 10 | 0 / 1 / 9 |
| 4 w | 0 / 2 / 8 | 0 / 0 / 10 | 0 / 0 / 10 |
| 7 w | 0 / 0 / 10 | 0 / 0 / 10 | 0 / 0 / 10 |
| 10 w | 0 / 0 / 10 | 0 / 0 / 10 | 0 / 0 / 10 |
| 13 w | 0 / 0 / 8 | 0 / 0 / 10 | 2 / 3 / 5 |
| 16 w | 1 / 0 / 9 | 0 / 1 / 9 | 0 / 0 / 10 |
| 20 w | 0 / 4 / 4 | 5 / 3 / 2 | 0 / 1 / 9 |
| 24 w | 0 / 3 / 7 | 9 / 0 / 1 | 7 / 3 / 0 |

HYBRIDOMA PRODUCING ANTIBODIES TO LAWSONIA INTRACELLULARIS

RELATED APPLICATIONS

This application is a divisional application of U.S. application Ser. No. 11/875,538, now U.S. Pat. No. 7,635,590, filed Oct. 19, 2007, which is a divisional application of U.S. application Ser. No. 11/158,800, now U.S. Pat. No. 7,303,891, filed Jun. 22, 2005, which claims priority to European Patent Application No. EP 04 014 804, filed Jun. 24, 2004 and European Application No. EP 04 027 193, filed Nov. 16, 2004, the contents of which are hereby incorporated by reference in their entirety.

FIELD OF THE INVENTION

The present invention relates to the field of animal health and in particular to *Lawsonia intracellularis*. In particular, the invention relates to a method of diagnosing *Lawsonia intracellularis* infection and a diagnostic test kit using *Lawsonia intracellularis*-specific antibodies. The invention also relates to the use of the method or test kit for diagnosing *Lawsonia intracellularis* infections.

BACKGROUND OF THE INVENTION

*L. intracellularis*, the causative agent of porcine proliferative enteropathy ("PPE"), affects virtually all animals, including humans, rabbits, ferrets, hamsters, fox, horses, and other animals as diverse as ostriches and emus. *L. intracellularis* is a particularly great cause of losses in swine herds in Europe as well as in the United States.

A consistent feature of PPE is the occurrence of intracytoplasmic, non-membrane bound curved bacilli within enterocytes in affected portions of intestine. The bacteria associated with PPE have been referred to as "*Campylobacter*-like organisms." S. McOrist et al., Vet. Pathol., Vol. 26, 260-264 (1989). Subsequently, the causative bacteria have been identified as a novel taxonomic genus and species, vernacularly referred to as Ileal symbiont (IS) intracellularis. C. Gebhart et al., Int'l J. of Systemic Bacteriology, Vol. 43, No. 3, 533-538 (1993).

More recently, these novel bacteria have been given the taxonomic name *Lawsonia (L.) intracellularis*. S. McOrist et al., Int'l. J. of Systemic Bacteriology, Vol. 45, No. 4, 820-825 (1995). These three names have been used interchangeably to refer to the same organism as further identified and described herein.

*L. intracellularis* is an obligate, intracellular bacterium which cannot be cultured by normal bacteriological methods on conventional cell-free media and has been thought to require attached epithelial cells for growth. S. McOrist et al., Infection and Immunity, Vol. 61, No. 19, 4286-4292 (1993) and G. Lawson et al., J. of Clinical Microbiology, Vol. 31, No. 5, 1136-1142 (1993) discuss cultivation of *L. intracellularis* using IEC-18 rat intestinal epithelial cell monolayers in conventional tissue culture flasks. In addition, H. Stills, Infection and Immunity, Vol. 59, No. 9, 3227-3236 (1991) discusses using Intestine 407 human embryonic intestinal cell monolayers and GPC-16 guinea pig colonic adenocarcinoma cell monolayers in conventional tissue culture flasks.

In particular, *L. intracellularis* can be cultivated be methods known in the art, preferably, according to U.S. Pat. Nos. 5,714,375 and 5,885,823. For example, culture cells may first be inoculated with an inoculum comprising *L. intracellularis* bacteria so as to infect the cells with the bacteria. Numerous cell lines can be used in practicing the invention, including, but not limited to, IEC-18 (ATCC 1589)—rat intestinal epithelial cells, HEp-2 (ATCC 23)—human epidermoid carcinoma cells, McCoys (ATCC 1696)—mouse (non-specified) cells, BGMK (Biowhittaker #71-176)—buffalo green monkey kidney cells, and swine intestinal epithelium cells. The preferred culture cells are HEp-2, McCoys or IEC-18 cells.

If culture cells are used, prior to being inoculated, the cells may be in the form of a monolayer. To form a monolayer, the cells may be seed into conventional flasks. Each flask is generally seeded with between about $1\times10^5$ cells to about $10\times10^5$ cells per 25, 75, 150, 850 $cm^2$ flask or roller bottle mixed with growth media. The growth media may be any media for cell cultivation which includes a nitrogen source, necessary growth factors for the chosen culture cells, and a carbon source, such as glucose or lactose. The preferred media is DMEM fortified with Ham's F 12 with 1-5% fetal bovine serum, although other commercially available media may be used with good results.

Successful cultivation of *L. intracellularis* is enhanced by maintaining the culture cells in a constant state of growth. Therefore, the culture cell monolayer should be at about 20 percent to about 50 percent confluency at the time of inoculation. Preferably, the cells should be at about 30 percent to about 40 percent confluency at the time of inoculation, most preferably at about 30 percent confluency.

Alternatively, the cells, prior to being inoculated, may be grown in suspension, as described infra. Preferably, the cells are first grown to 100% confluency in the form of a monolayer in an adherent type system, e.g., a roller bottle system, and then transferred to 3-3000 liters and grown in suspension.

The inoculum may be a culture of *L. intracellularis* obtained from infected swine or other animals.

The inoculum can be an intestinal homogenate prepared by scraping the mucosa off of the ileum of a swine or other animal infected with PPE. When preparing an intestinal homogenate, ileal sections selected for culture should show severe lesions with gross thickening of the gut. Due to the fragile nature of the bacteria, samples should preferably be stored at −70° C. as quickly as possible after necropsy. An antibiotic to which *L. intracellularis* is resistant such as Vancomycin, Amphotericin B or members of the aminoglycoside group of antibiotics, including Gentamicin and Neomycin, to name a few, is preferably added to the inoculum to suppress contaminating bacteria while permitting *L. intracellularis* growth. Whether the inoculum is a pure culture or an intestinal homogenate, inoculation of the culture cells can be performed by various techniques known in the art, given the teachings herein.

The bacteria and/or inoculated culture cells are then incubated under a reduced dissolved $O_2$ concentration. At dissolved oxygen concentrations greater than 10% *L. intracellularis* growth is less than optimal with cessation of growth eventually occurring at oxygen concentrations outside this range. Preferably, the bacteria and/or inoculated culture cells are incubated in a dissolved oxygen concentration in the range of about 0% to about 10%. More preferably, the bacteria and/or cells are incubated in an oxygen concentration in the range of about 0% to about 8%, with an oxygen concentration of about 0% to about 3.0% being most preferred.

The proper concentration of carbon dioxide is also important to the proper growth of *L. intracellularis*. At carbon dioxide concentrations greater than 0% and less than 4%, non-optimum growth occurs with cessation of growth eventually occurring at carbon dioxide concentrations outside this range. Preferably, the carbon dioxide concentration is in the range from about 6% to about 10%, with a carbon dioxide concentration of about 8.8% being most preferred.

In addition, the cells are preferably incubated at a hydrogen concentration in the range from about 73% to about 96%. Nitrogen may be used in place of some or all of the hydrogen present. Most preferably, the cells are incubated in about 0 to about 8.0% $O_2$, about 8.8% $CO_2$, and about 83.2% $H_2$.

Inoculated cells may be incubated in a dual gas incubator or other gas chambers which contains the proper hydrogen, oxygen and carbon dioxide concentrations and which allows the cells to be suspended during incubation. The chamber should comprise a means for maintaining the inoculated cells in suspension, and a gas monitor and supply source to supply and maintain the proper gas concentrations. The incubation temperature should be in the range of from 30° C. to about 45° C. and is more preferably in the range of from about 36° C. to about 38° C. Most preferably, the temperature is about 37° C. The necessary equipment for cultivation and attenuation is readily available to those or ordinary skill in the art given the teachings herein. One example of equipment suitable for carrying out the resent invention is a dual gas incubator, e.g., model 480 (Lab-Line, Melrose Park, Ill.) in conjunction with spinner flasks to maintain the cells in suspension. The presently preferred equipment comprises a fermentor, bioreactor, stir plate or rotary shaker containing media and capable of maintaining the culture cells in suspension via sparging gas of the appropriate concentration, or other means of mechanical agitation, and continuously monitoring dissolved $O_2$ levels in the media. New Brunswick, Braun and other companies make suitable fermentors and bioreactors for this purpose.

By maintaining the inoculated cells in a suspended state during incubation, maximum growth of the cells, and hence *L. intracellularis*, is achieved by increasing each individual cell's exposure to growth media and the proper mixture of hydrogen, oxygen and carbon dioxide. The culture cells can be agitated and maintained in suspension by a variety of methods known in the art including, for example, culture flasks, roller bottles, membrane cultures, biobags, WAVE™ bioreactor systems, and spinner flasks. The cells may be kept in suspension during incubation by incubating the cells in a spinner flask inside a dual gas incubator or similar apparatus. The term "spinner flask", as used herein, means a flask or other container which employs a paddles, propeller or other means to agitate the culture and keep the cells contained therein in suspension.

Alternatively, the inoculated cells are incubated until the cells reach confluency and then the cells are placed in a spinner flask containing growth media and incubated in a dual gas incubator while spinning the flask. Preferably, the inoculated cells are scraped or trypsinized and passaged into the spinner flask. This can be achieved by a variety of methods known in the art such as using a cell scraper to detach the cells. Once the cells are introduced into the spinner flask, the paddle of the spinner flask is typically rotated in the range of from about 30 to about 60 rpm on a magnetic stir plate in order to maintain the infected cells in suspension.

A portion of the cultivated *L. intracellularis* is then passaged to fresh culture to increase the production of *L. intracellularis* bacteria. The term "passaging" or variations thereof herein means the process of transferring a portion of the cultivated *L. intracellularis* to fresh culture cells in order to infect the fresh cells with the bacterium. The term "fresh", as used herein, means cells which have not yet been infected by *L. intracellularis*. Preferably such cells are on the average no more than approximately one day old.

The passage of *L. intracellularis* in suspension cultures may be accomplished by removing a portion of the original culture and adding it to a new flask containing fresh culture cells. If the original culture has a high number of bacteria/ml, for example, greater than about $10^4$ bacteria/ml, it is preferable to add between about 1 to 10% (volume to volume) of culture from the infected flask to a new flask containing fresh cells. This is preferably done when 50-100% of the cells are infected. If fewer than 50% of the cells are infected, passaging is preferably accomplished by splitting the culture 1:2 into a new flask and scaling-up the volume by adding fresh media. In either case, cell lysis and other steps are not required, in direct contrast to the passage of monolayer cultures, as in the prior art.

After sufficient growth of the culture cells and subsequent infection by *L. intracellularis*, as determined by indirect fluorescent antibody (IFA) staining, $TCID_{50}$ or another comparable method, at least a portion of the cultivated *L. intracellularis* bacteria is then harvested. The harvesting step may be performed by separating the bacteria from the suspension by various techniques known to those of ordinary skill in the art, given the teachings herein. Preferably, the *L. intracellularis* bacteria is harvested by centrifuging the contents of all or a portion of the suspension to pellet the culture cells, resuspending the resulting cell pellets, and lysing the infected cells. Typically, at least a portion of the contents is centrifuged at about 3000×g for about 20 minutes in order to pellet the cells and bacteria. The pellet may then be resuspended in, for example, a sucrose-phosphate-glutamate (SPG) solution and passed approximately 20 times through a 25 gauge needle in order to lyse the cells. If further purification is desired, the samples can be centrifuged at about 145×g for about five minutes to remove cellular nuclei and debris. The supernatant may then be centrifuged at about 3000×g for about twenty minutes and the resulting pellet resuspended in an appropriate diluent, such as SPG with fetal bovine serum (to prepare harvested bacteria suitable for lyophilization, freezing, or use as an inoculant) or growth media (to prepare harvested bacteria more suitable for passaging to fresh cells).

As previously mentioned, effective growth of *L. intracellularis* for large-scale production is enhanced by keeping the tissue cells actively growing. Using suspension cultures greatly facilitates keeping the cells actively growing and permits continuous culture expansion and scale-up. Using a fermentor and between about 0 to 3% dissolved $O_2$ as explained above, enables growth of up to $10^8$ bacteria/ml.

When using McCoys or IEC-18 cells, it is preferable to add gelatin, agarose, collagen, acrylamide or silica beads, such as Cultisphere-G porous microcarriers (HyClone Laboratories, Logan Utah), along with the growth media. However, HEp-2 cells and others do not require microcarriers according to the methods used herein.

For culture maintenance purposes, with HEp-2 cultures, preferably 25% to 50% of the culture is removed and replaced with fresh media at weekly intervals. For cell cultures with microcarriers or beads, preferably 25% to 50% of the culture is removed and replaced with fresh media 1-2 times weekly. For scale-up purposes, an additional 25% to 50% of media, or media with microcarriers, may be added to the culture.

Depending upon the rate at which the culture cells become infected, passage to fresh cells generally occurs between about every 2 to about 7 days. Assuming that the culture cells become at least 70% infected within 2 to 7 days, preferably passage occurs between about every 5 to 7 days.

Diagnosis of *L. intracellularis* antigen is carried out today by using direct immunofluorescence and PCR. Diagnosis of antibodies specific to *L. intracellularis* is carried out today by using immuno-fluorescence. These methods are laborious and time consuming and are not suitable for large scale screenings.

Effective diagnosis of PPE has also been hindered by the time required to culture the causative bacteria. As a result of the present invention, development of diagnostic tools promoting rapid and accurate assays for the presence of *L. intracellularis* in biological samples taken from swine and other animals susceptible to PPE is now possible.

Therefore, the technical problem underlying the present invention is to provide improved methods for diagnosis of *L. intracellularis* disease.

BRIEF SUMMARY OF THE INVENTION

The present invention relates to the field of animal health and in particular to *Lawsonia intracellularis*. In particular, the invention relates to a method of diagnosing *Lawsonia intracellularis* infection and a diagnostic test kit using *Lawsonia intracellularis*-specific antibodies. The invention also relates to the use of the method or test kit for diagnosing *Lawsonia intracellularis* infections.

DETAILED DESCRIPTION OF THE INVENTION

Definitions of Terms Used in the Description

Before the embodiments of the present invention it must be noted that as used herein and in the appended claims, the singular forms "a", "an", and "the" include plural reference unless the context clearly dictates otherwise. Thus, for example, reference to "a bacterium" includes a plurality of such bacteria, reference to the "cell" is a reference to one or more cells and equivalents thereof known to those skilled in the art, and so forth. Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies as reported in the publications which might be used in connection with the invention. Nothing herein is to be construed as an admission that the invention is not entitled to antedate such disclosure by virtue of prior invention.

As used herein, the term "*L. intracellularis*" means the intracellular, curved gram-negative bacteria described in detail by C. Gebhart et al., Int'l J. of Systemic Bacteriology, Vol. 43, No. 3, 533-538 (1993) and S. McOrist et al., Int'l J. of Systemic Bacteriology, Vol. 45, No. 4, 820-825 (1995), each of which is incorporated herein by reference in their entireties; the causative bacteria which can be obtained from PPE infected swine or other animals throughout the world given the knowledge in the art and the teachings herein; and variants or mutants of any of the above bacteria, whether spontaneously or artificially obtained and DNA, RNA and bacterial proteins specific for *L. intracellularis*, including proteins expressed in vectors or after in vivo application, and also fragments or antigenic derivatives of *L. intracellularis*. This term also includes adapted isolates and attenuated isolates as defined below.

As used herein, the term 'adapted isolate' means any *L. intracellularis* isolate that is prepared according to the cultivation and passaging techniques in cell culture or any other technique to replicate *L. intracellularis* for purposes of antigen preparation.

As used herein, the term "attenuated isolate" means any *L. intracellularis* isolate that is prepared according to the cultivation and passaging techniques taught herein to achieve avirulence while maintaining immunogenic properties when administered to a host animal.

As used herein, the term "large-scale cultivation" means a level of cultivation of *L. intracellularis* greater than approximately 2.0 to 3.0 liters and includes production on a scale of 100 liters or more. "Cultivation" as used herein, means the process of promoting the growth, reproduction and/or proliferation of *L. intracellularis*.

DISCLOSURE OF THE INVENTION

The solution to the above technical problem is achieved by the description and the embodiments characterized in the claims.

The aim of the present invention is to provide a method of diagnosing pre-clinical or clinical *L. intracellularis* infection. Furthermore, an immune response to *L. intracellularis* shall be detected and a tool for *L. intracellularis* epidemiology is to be provided.

This objective has been achieved according to the present invention within the scope of the specification and claims by means of a method of diagnosing pre-clinical or clinical *L. intracellularis* infection.

The invention relates to the detection of antibodies against *L. intracellularis* and to the detection of *L. intracellularis* itself. Such antibodies include any antibody type known to the skilled person, in particular immunoglobulins of the subtypes IgA, soluble IgA, IgM, IgG (IgG1, IgG2a, IgG2b, IgG3), and also IgD, IgE.

To detect antibodies specific for *L. intracellularis*, according to the invention, the method is based on the fact that
a) a liquid sample is taken from a mammal
b) the specific binding of such liquid sample to *L. intracellularis* antigen is detected
c) the result obtained is compared with a control.

As defined above, *L. intracellularis* also includes fragments or antigenic derivatives of *L. intracellularis*, which may be used in a method as above.

Similarly, according to the invention, to detect *L. intracellularis*, the method according to the invention is as follows:

the method is based on the fact that
a) a liquid sample is taken from a mammal
b) the specific binding of such liquid sample to *L. intracellularis* antibodies is detected
c) the result obtained is compared with a control.

The liquid sample may include any bodily fluid including saliva, sweat, urine, blood, secretions, excretions or other bodily fluid samples known to the expert in the field. In a preferred embodiment, the liquid sample is collected using either a collection container (for urine or other liquid), a syringe/collection tube (for blood) or some type of collection swab (for saliva, sweat etc.) Preferably, if the sample in step a) is blood, serum or plasma is isolated from this blood sample and step b) is carried out with serum or plasma instead of the liquid sample. Subsequently, step c) is carried out as above.

In a preferred embodiment, the method is an immune test. An immune test uses monoclonal antibodies or polyclonal antisera specific to *L. intracellularis*. Immune tests according to the invention include the methods of detection known in the art such as the ELISA test (enzyme-linked immuno-sorbent assay) or the so-called sandwich-ELISA test, dot blots, immunoblots, radioimmuno tests (radioimmunoassay RIA), diffusion-based Ouchterlony test or rocket immunofluorescent assays. Other immune tests are the indirect or direct immunofluorescent antibody test ("IFA"). Another immune test is the so-called Western blot (also known as Western transfer procedure or Western blotting). The purpose of Western blot is to transfer proteins or polypeptides separated by polyacrylamide gel electrophoresis onto a nitrocellulose filter or other suitable carrier and at the same time retain the relative positions of the proteins or polypeptides obtained from the gel electrophoresis. The Western blot is then incubated with an antibody which specifically binds to the protein or polypeptide under consideration. These methods of detection can be used by the average skilled person to perform the invention described herein. Literary references in which the skilled person can find the above-mentioned methods and other detection methods are listed as follows: *An Introduction to Radioimmunoassay and Related Techniques*, Elsevier Science Publishers, Amsterdam, The Netherlands (1986); Bullock et al., *Techniques in Immunocytochemistry*, Academic Press, Orlando, Fla. Vol. 1 (1982), Vol. 2 (1983), Vol. 3 (1985); Tijssen, *Practice and Theory of Enzyme Immunoassays: Laboratory Techniques in Biochemistry and Molecular Biology*, Elsevier Science Publishers, Amsterdam, The Netherlands (1985). Solid and fluid protein chip technologies or microarray technologies using labeled or unlabeled reagents are further immune tests according to the invention. Such test are widely described, for example by Kozak K R, et al., *Identification of biomarkers for ovarian cancer using strong anion-exchange Protein Chips: potential use in diagnosis and prognosis* . . . Proc Natl Acad Sci USA. 2003 Oct. 14; 100(21):12343-8 (2003), or by Fulton, R. J., et al., *Advanced multiplexed analysis with the FlowMetrix™ system. Clinical Chemistry* 43 (9), 1749-1756 (1997).

The invention further relates to a diagnostic test kit for detecting *L. intracellularis* infection which contains all the elements required to carry out a method of diagnosing preclinical or clinical *L. intracellularis* infection as described herein.

The invention further relates, in particular, to a diagnostic test kit which contains antibodies specific to *L. intracellularis*.

The invention further relates, in particular, to a diagnostic test kit, characterised in that the antibodies according to the invention are polyclonal.

The invention further relates, in particular to a diagnostic test kit, characterised in that the antibodies according to the invention are monoclonal.

A diagnostic test kit is a collection of all the components for a method of diagnosis according to the invention. Some examples (not an exhaustive list) of other elements for performing a process according to the invention include containers such as 96-well plates or microtitre plates, test tubes, other suitable containers, surfaces and substrates, membranes such as nitrocellulose filter, washing reagents and buffers. A diagnostic test kit may also contain reagents which may detect bound antibodies, such as for example labelled secondary antibodies, chromophores, enzymes (e.g. conjugated with antibodies) and the substrates thereof or other substances which are capable of binding antibodies.

The *L. intracellularis* bacteria as disclosed herein or known in the art, or components derived from such bacteria, can be used as an antigen in an ELISA or other immunoassay, such as an immunofluorescent antibody test ("IFA"), to detect antibodies to *L. intracellularis* in the serum and other body fluids of animals suspected of being infected with the bacteria. The presently preferred immunoassay is an IFA as described in the example below. Alternatively, the bacteria of the instant invention can be used in a Western Blot assay.

The preferred Western Blot protocol is as follows:
1. Run antigen on 12% SDS-PAGE and transfer to nitrocellulose membrane.
2. Place membrane in blocking buffer for 2 hours.
3. Remove blocking buffer and rinse with PBS for 1 minute.
4. Dilute serum in blocking buffer and add to membrane. Incubate for 2 hours at room temperature.
5. Wash 3 times with wash buffer (5 minutes for each wash).
6. Dilute a conjugated anti-*L. intracellularis* specific antibody, preferably a monoclonal antibody, in blocking buffer and add to membrane. Incubate for 1 hour at room temperature.
7. Wash 3 times with wash buffer.
8. Add substrate for 10 minutes or until strong banding occurs.
9. Rinse with PBS.
10. Air dry and store in the dark.

The conjugate linked to the antibody could be for example an enzyme, such as a. horse radish peroxidase (HRP) or alkaline phosphatase (AP). Alternatively, a chromophore, or any other detectable substance which is can be quantified in the presence of a substrate, can be used as conjugate.

The most preferred immune test according to the invention is an ELISA.

Most preferably, such ELISA is a sandwich ELISA (=capture ELISA). Such an ELISA is more specific, as it detects with two antibodies specific to two different epitopes on the same antigen. In a sandwich ELISA, unlabelled antibodies are coated to the microtiter plates. The *L. intracellularis* as antigen is subsequently added. After a washing step, the bound *L. intracellularis* antigen is detected with a second, labeled, *L. intracellularis*-specific antibody reactive to a different epitope on *L. intracellularis*.

An exemplary coating procedure is as follows:

The plates are coated with unlabelled antibody, e.g. in 10% Sucrose/10% Normal Horse Serum in ddH$_2$O and incubated with *Lawsonia intracellularis* antigen. The plates are then dried and sealed and stored at 37° C. Alternatively, the antibody coated plates are stored and the antigen is added when the ELISA is conducted.

A preferred ELISA protocol according to the invention is as follows (use of antibody coated plates):
1. Add 0.1 ml/well antigen diluted in coating buffer. Incubate for 18 hours at 4° C.
2. Wash 3 times with PBS.
3. Add 0.25 ml of blocking buffer to each well of plate. Incubate 1 to 2 hours at 37° C.

4. Wash 3 times with wash buffer.
5. Dilute serum in blocking buffer and add 0.1 ml to the first wells of plate. Make serial 1:2 dilutions across the plate. Incubate for 1 hour at 37.
6. Wash 3 to 5 times with wash buffer.
7. Dilute a conjugated anti-*L. intracellularis* specific antibody, preferably a monoclonal antibody, in blocking buffer and add 0.1 ml to wells of plate and incubate for 1 hour at 37° C.
8. Wash 3 to 5 times with wash buffer.
9. Add substrate.
10. Measure absorbance of light with a spectrophotometer.
11. Wells in which antigen was not added are used as blanks.
12. Positive and negative control swine serum should also be used with each test.

A preferred ELISA is carried out as follows:

The plates are coated with unlabelled antibody, e.g. in 10% Sucrose/10% Normal Horse Serum in ddH$_2$O and incubated with *Lawsonia intracellularis* antigen. The plates are then dried and sealed and stored at 37° C.

1. Add 90 µl buffer into all wells.
2. Add 10 µl serum into selected wells.
3. Incubate plate for 1 hour at 37 C.
4. Wash plate 3 times with PBST.
5. Add HRP conjugated anti-*L. intracellularis* specific antibody, preferably a monoclonal antibody diluted in CDS-C+0.5M NaCl, 100 µl/well.
6. Incubate plate for 1 hour at 37 C.
7. Wash plate 3 times with PBST.
8. Add substrate, 100 µl/well and incubate at room temperature for 10 minutes.
9. Add 50 µl stop/well.
10. Read the plate at 450 nm in a spectrophotometer.

The most preferred sandwich ELISA protocol according to the invention is as follows:

1. Add 0.1 ml/well mAb diluted in coating buffer. Incubate for 18 hours at 4° C.
2. Wash 3 times with PBS.
3. Add 0.1 ml/well antigen diluted in buffer to each well of plate. Incubate 1 to 2 hours at 37° C.
4. Wash 3 times with wash buffer and/or directly add 0.25 ml of blocking buffer to each well of plate. Incubate 1 to 2 hours at 37° C.
5. Wash 3 times with wash buffer.
6. Dilute serum in blocking buffer and add 0.1 ml to the first wells of plate. Make serial 1:2 dilutions across the plate. Incubate for 1 hour at 37.
7. Wash 3 to 5 times with wash buffer.
8. Dilute conjugated anti-*L. intracellularis* specific antibody, preferably a monoclonal antibody in blocking buffer and add 0.1 ml to wells of plate and incubate for 1 hour at 37° C.
9. Wash 3 to 5 times with wash buffer.
10. Add substrate.
11. Measure absorbance of light with a spectrophotometer.
12. Wells in which antigen was not added are used as blanks.
13. Positive and negative control swine serum should also be used with each test.

Antigen as used herein is *L. intracellularis* as defined above. mAb relates to a monoclonal antibody specific for *L. intracellularis*. Preferably, such antibody is an antibody as disclosed below.

Surprisingly, outstanding antibodies were generated to be used in the ELISA according to the invention. The antibodies have the following reference numbers: 301:39, 287:6, 268:29, 110:9, 113:2 and 268:18. All antibodies are specific for antigens of *L. intracellularis* bacteria. Preferably as capture antibodies in a sandwich ELISA are 110:9, 113:2 or 287:6, and as conjugated antibodies 268:18, 268:29 or 287:6. Most preferred as capture antibody is antibody 110:9 and as conjugated antibody is antibody 268:29.

The antibodies according to the invention are produced by hybridoma cells. Said hybridoma cells according to the invention were deposited by Dr. M. Merza, who may be contacted at Ingelheim AM Rhein, D-55216, Germany, at the Centre for Applied Microbiology and Research (CAMR) and European Collection of Cell Cultures (ECACC), Salisbury, Wiltshire SP4 0JG, UK, as patent deposit according to the Budapest Treaty. The date of deposit was Sep. 22, 2004. HYBRIDOMA CELL LINE 110:9 is successfully deposited under ECACC Acc. No. 04092204. HYBRIDOMA CELL LINE 113:2 is successfully deposited under ECACC Acc. No. 04092201. HYBRIDOMA CELL LINE 268:18 is successfully deposited under ECACC Acc. No. 04092202. HYBRIDOMA CELL LINE 268:29 is successfully deposited under ECACC Acc. No. 04092206. HYBRIDOMA CELL LINE 287:6 is successfully deposited under ECACC Acc. No. 04092203. HYBRIDOMA CELL LINE 301:39 is successfully deposited under ECACC Acc. No. 04092205. All the above deposits were tested and confirmed to be viable and capable of reproduction on Sep. 22, 2004. The deposition will irrevocably remove all restrictions on the availability of the deposited material to the public upon the granting of patent based on the present application.

The present invention is further described in the following examples which are provided for illustrative purposes only and are not to be construed as limiting. Indeed, other variants of the invention will be readily apparent to one of ordinary skill in the art.

All publications and patents cited herein are incorporated by reference in their entireties.

EXAMPLES

Example 1

1.0 Material anti-Lawsonia hybridomal celline: 372:13, 113:2, 268:18, 287:6, 110:9, 268:29, 301:39.

Equipment and media for hybridomal cell cultivation.

Equipment and buffers for purification and HRP conjugation of monoclonal antibodies (mAb).

Equipment and solutions for ELISA

*Lawsonia* antigen SF 1289 N343 Dec. 20, 2000

*Lawsonia* positive sera: lot#052902pig#26 (experimentally infected), lot#052902pig#69 (vaccinate)

*Lawsonia* negative sera: p 25.8#273 Day 52 Jun. 30, 1995 116705

1.1 Methods

The preparation of the monoclonal antibodies was performed according to standard operating procedures at Svanova Biotech.

1.1.1 Culturing of Hybridomal Cells and Preparation of HRP Conjugated Monoclonal Antibodies To secure the hybridomal cell-lines 15 vials of each cell line was prepared and stored in −135° C.

One vial of each hybridomal cell-line was thawed and the cells were grown in cell-culture flasks.

500 ml to 1000 ml of supernatant from each cell line was purified and conjugated to horse-radish peroxidase.

1.1.2 Blocking ELISA

The purified and HRP conjugated mAb's were tested for their ability to be blocked by positive *Lawsonia* pig sera in ELISA.

The ELISA plate was coated with *Lawsonia* antigen in a dilution of 1/200, 100 µl/well The pig sera was diluted 1/10, 100 µl/well The HRP conjugated mAb's were diluted and added, 100 µl/well.

The results are expressed as Percent inhibition (PI) according to the following formulae:

$$PI = 1 - (OD\ sample/OD\ mAb) \times 100.$$

1.2 Results 1.2.1 Culturing of Hybridoma Cells and Preparation of HRP Conjugated Monoclonal Antibodies All but one of the mAb's were successfully purified and HRP conjugated. They had good production capacity.

mAb 372:13 had poor production capacity. This mAb was not successfully HRP conjugated and was therefore not tested in the blocking ELISA.

1.2.2 Blocking ELISA

Two positive (#26, #69) and two negative (25.8#273, 116705) sera were used in the experiments.

The experimentally infected sera (#26) inhibited all the six HRP conjugated mAb's, but in different levels. The sera from a vaccinated pig inhibited the mAb's to a much lesser extent.

The negative sera showed no or very low inhibition.

Figure 1:
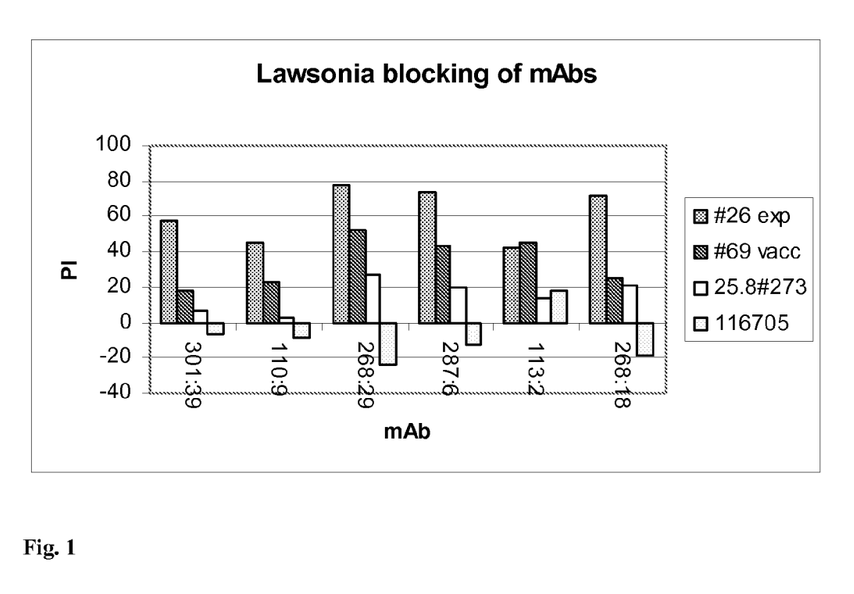
FIG. 1: Results of Blocking ELISA according to the invention

The results are presented in the table below and in FIG. 1.

|  | mAb | | | | | |
|---|---|---|---|---|---|---|
| Serum | 301:39 | 110:9 | 268:29 | 287:6 | 113:2 | 268:18 |
| #26 exp + | 57 | 45 | 78 | 74 | 42 | 72 |
| #69vacc + | 18 | 23 | 52 | 43 | 45 | 25 |
| 25.8#273 − | 7 | 3 | 27 | 20 | 14 | 21 |
| 116705 − | −7 | −9 | −24 | −13 | 18 | −19 |

1.3 Discussion

The results of this study clearly show that one or more of the monoclonal antibodies tested are suited for a blocking ELISA test against *Lawsonia intracellularis*. MAb 268:29, 287:6 and 268:18 show the clearest distinction between the positive and negative sera i.e. are strong candidates in the development of the blocking ELISA.

Example 2

2.0 Summary

Development and establishment of a sandwich b-ELISA prototype for the detection of antibodies to *Lawsonia intracellularis*:

After calculation of sensitivity and specificity by using immunoflourescence test IFA as gold standard the following can be concluded:

Capture mAb 110:9 gives a clear distinction between positive and negative samples.

Detection mAb 268:29 HRP gives a clear distinction between positive and negative sera showing a sensitivity and specificity of 100%.

It is recommended that the prototype will be as follows:

mAb 110:9 as capture mAb, coated in Nunc maxi-sorp strips C-8

Antigen (Ag): *Lawsonia intracellularis* culture (preferably the concentrated material produced in R&D at BI)

Serum samples diluted 1/10 in 0.5M NaCl/PBST. Incubation for 1 hour at 37 C.

HRP conjugated mAb 268:29, lyophilized in CDS-C buffer containing 0.5M NaCl. Incubation for 1 hour at 37 C.

Substrate K-Blue Max, incubation for 10 minutes at room temperature.

Svanova's stop solution 2.1 Material and Methods

The ELISA was performed according to the following procedure:

2.1.0 ELISA Procedure

Add 90 µl buffer into all wells.

Add 10 µl serum into selected wells.

Incubate plate for 1 hour at 37 C.

Wash plate 3 times with PBST

Add HRP conjugate mAb diluted in CDS-C+0.5M NaCl, 100 µl/well.

Incubate plate for 1 hour at 37 C.

Wash plate 3 times with PBST.

Add substrate, 100 µl/well and incubate at room temperature for 10 minutes.

Add 50 µl stop/well

Read the plate at 450 nm in a spectrophotometer.

The results were presented as 1—OD values or 2—PI (percent inhibition) values i.e. 100—sample OD/mAb OD×100.

2.1.1 Test 1 (ELISA 030922, 030923×2)

C-8 maxi strips coated with mAb 110:9, 113:2, 301:39, 287:6, 268:29, 300 ng/well Blocking of strips with 10% 2251HÄS (normal horse serum), 10% sucrose/UHP H₂O. 150 µl/well, incubated for 30 seconds at room temperature.

Ag #030619 diluted 1/10 in PBST, 100 µl/well, 3 hours incubation in 4 C.

Strips dried in 37 C for 3 hours. Kept in 4 C.

Sera: IFA pos: #26, #69. IFA neg: #6, C1, D1, E1. Diluted 1/10 in 0.5M NaCl/PBST Conjugate: 268:18, 113:2, 301:39110:9, 287:6, 268:29 HRP diluted in 0.5M NaCl/PBST.

All capture mAb's were tested against all HRP conjugated mAb except against its own.

2.1.2 Test 2 (ELISA 030924)

Strips coated with 110:9, 113:2 and 287:6 according to test 1 above.

Sera: IFA pos: #26, #69. IFA neg: #6, C1, D1, E1. Diluted 1/10 in 0.5M NaCl/PBST HRP Conjugate mAb 268:18, 268:29, 287:6 diluted in 0.5M NaCl/CDS-C (standard buffer for lyophilizing of conjugates as Svanova in production).

2.1.3 Test 3 (ELISA 030925)

Strips coated with 110:9, 113:2 and 287:6 according to test 1 above.

Sera: 24 sera (10 IFA pos, 10 IFA neg and 4 doubtful) were tested. Dilution: 1/10 in 0.5M NaCl/PBST.

Conjugate: 268:18 HRP diluted in 0.5M NaCl/CDS-C.

2.1.4 Test 4 (ELISA 030930, 031002, 031008)

Strips coated with 110:9 according to test 1 above.

Sera: 21 IFA positive and 69 IFA negative. Dilution: 1/10 in 0.5M NaCl/PBST

Conjugate: 268:18 conjugated with HRP and 268:29 conjugated with HRP diluted in 0.5M NaCl/CDS-C.

2.2 Results 2.2.1 Test 1 (ELISA 030922, 030923×2)

Capture mAb 110:9, 113:2 and 287:6 with conjugates 268: 18 and 268:29 and 287:6 seems to be the best candidates for the sandwich b-ELISA as these combinations showed the best blocking capacity on the positive sera. Sera no #6 scored positive in most of the tests. This was suspected as this sera also scored positive in the previously developed b-ELISA prototype.

2.2.2 Test 2 (ELISA 030924)

This test was mainly performed to assure that the standard buffer used to lyophilizing of the conjugate could be used. The results show that blocking was achieved with the positive sera. The best blocking was found with detection mAb 268:18 or 268:29.

2.2.3 Test 3 (ELISA 030925)

The capture mAb 110:9 was found to be the best choice as it gave the clearest differentiation between positive and negative samples.

2.2.4 Test 4 (ELISA 030930, 031002. 031008)

Obtained OD and PI values can be found in appendix 5. When plotting the OD values against the IFA results HRP conjugated mAb 268:29 gives the clearest distinction between positive and negative samples with a 100% sensitivity and specificity. mAb 268:18 also gives a sensitivity and specificity of 100% but the area between positive and negative samples is slight. When plotting the PI values mAb 268:18 gives a sensitivity of 95.7 and specificity of 100% at cut-off 20.9 while mAb 268:29 gives both a sensitivity and specificity of 100% at cut-off 28.6

2.3. Discussion

After calculation of sensitivity and specificity against the immunoflourescence test IFA the following can be concluded:

Capture mAb 110:9 is the best choice as it gives a clear distinction between positive and negative samples.

Detection mAb 268:29 conjugated with HRP is the best choice as it gives a clear distinction between positive and negative sera with a sensitivity and specificity of 100%.

It is recommended that the prototype will be as follows:

mAb 110:9 as capture mAb, coated in Nunc maxi-sorp strips C-8

Ag: *Lawsonia intracellularis* culture (preferably the concentrated material produced in R&D at BI)

Serum samples diluted 1/10 in 0.5M NaCl/PBST. Incubation for 1 hour at 37 C.

HRP conjugated mAb 268:29, lyophilized in CDS-C buffer containing 0.5M NaCl. Incubation for 1 hour at 37 C.

Substrate K-Blue Max, incubation for 10 minutes at room temperature.

Svanova's stop solution

Example 3

3.1 Summary

The performed accelerated stability studies indicate that the *Lawsonia intracellularis* antigen captured ELISA plate has a stability of at least one year and that the a-*Lawsonia* HRP conjugate 268:29 has a stability of 6 to 12 months in a lyophilized form.

3.2 Introduction

In order to estimate the stability of the components of a future *Lawsonia intracellularis* ELISA kit accelerated stability tests has to be performed. The component to be tested is stored at 37 C for 4 weeks and is thereafter tested in the ELISA in comparison with a component kept at 4 C. 4 weeks stability in 37 C indicates a shelf-life of about 12 months. This report describes accelerated stability studies performed on the antigen captured ELISA plate and on the HRP conjugate.

3.3 Materials and Methods

Accelerated Stability on Plates (ELISA 031024)

Plates were coated with Lawsonia mAb 110:9 blocked with 10% Sucrose/10% Normal Horse serum in ddH$_2$O and incubated with Lawsonia antigen. Plates were dried and sealed and put in +37° C. Plates were taken from +37 C weeks 1, 2, 3 and 4 and stored in a refrigerator. Plates were also stored in +4 C for the whole test-period as a reference.

Positive sera #26, #69 and #06 and negative C2, D1 and E2 were used to check the performance of the sandwich ELISA. HRP conjugated mAb 268:29 lot #030120 was used.

Accelerated Stability on Lyophilized Conjugate (ELISA 031027)

HRP conjugated mAb 268:29 lot #030120 was diluted 1/1000 in CDS-C buffer dispensed into glass bottles and lyophilized according to standard procedures. Four lyophilized bottles were stored at +37 C for 1, 2, 3 and 4 weeks. Bottles were also stored at 4 C. The different bottles were tested in the sandwich ELISA.

As positive serum #26 was used and negative serum 030926 were used. It was found that a dilution of 1/1000 of the conjugated antibody ("conjugate dilution") gave too high OD values in the test. The conjugated antibody was therefore titrated in the plate to obtain a correct signal for the test.

3.4. Results

Accelerated Stability on Plates

A big drop in OD values were seen after week 1 compared to the OD value from the strips kept in +4° C. No big differences were seen when comparing week 1 to 4.

When looking at the PI values no significant was found between week 1 through 4 and +4° C.

Accelerated Stability on Lyophilized Conjugate

At a "conjugate dilution" of 1/8000 serum #26 showed a decrease from 0.547 to 0.398 after 4 weeks and serum 030926 dropped from 1,654 to 0.99 after the 4 week period.

3.5. Discussion

The performed accelerated stability studies indicate that the *Lawsonia intracellularis* ELISA plate has a stability of at least one year. The anti-*Lawsonia* HRP conjugated 268:29 antibody showed a 40% decrease in OD value against the negative sera and after 4 weeks. This might indicate some instability of the conjugate. When calculating on the OD values a 40% decrease of a signal at 1.5 means and OD value of 0.9 after 1 year which is still within the acceptance criteria.

Example 4

4.1. Summary

The verification of the prototype (plate batch 040107) was performed by testing 50 sera previously used when developing the prototype. The verification study showed a 100% agreement with the positive sera while 2 of the 25 negative sera scored positive in the verified batch.

It was found that normal horse serum can be used in the CDS-C buffer instead of swine sera which is the case today.

It was found that PBST containing 0.042% PVP showed similar results as using the PBST tablets (that contains PVP).

4.2. Introduction

In order to verify the sandwich ELISA prototype a larger number of sera have to be tested on a large scale produced plate batch. The study was performed on plate batch 040107 that was tested by examining 50 serum samples that had previously been used to develop the prototype.

Buffer CDS-C is used as preservative when lyophilizing the HRP conjugate. This buffer contains swine sera. As it can be problematic in the future to find Lawsonia negative sera to be used in the CDS-C buffer an alternative has to be tested. In this study normal horse serum and foetal bovine serum were tested.

The majority of the laboratory work on this ELISA has been performed with PBST tablets. It has been seen that the 20× conc. PBST that is included in Svanovir kits can not be used since the test will then not correctly differentiate between positive and negative samples. When comparing the recipes of the tablets and the 20×conc. PBST it was found that all components were the same except for 0.042% PVP (Polyvinylpyrrolidone K25) that was included in the tablets as a stabilizing factor. Experiments showed that when adding the PVP to the 20×PBST the same results as the tablets will be achieved.

4.3. Materials and Methods

Verification of Prototype (ELISA 040312)

50 sera (received from Bioscreen) previously tested in the prototype ELISA was tested on the large scale plate batch #040107. PBST 20× conc buffer with 0.042% PVP was used. Lyophilized conjugate batch 040308 was used.

CDS-C Buffer with Normal Horse Serum

Test ELISA 040203

CDS-C buffer was prepared with; 1—swine serum (as in TJ4/05F), 2—with normal horse serum and 3—with foetal bovine serum. The buffers were tested as conjugate buffer in the ELISA. Serum tested were gris 2, 4, 13 and 17, 1-29664, 3-29664, A-27239, B-27239, #26 and C2. HRP conjugated mAb 268:29 lot #030318 was used. 20× conc PBST with 0.042% PVP was used Test ELISA 040311

CDS-C buffer containing normal horse serum has been used to prepare lyophilized conjugate at two occasions (040211, 040308). The conjugate was prepared to obtain a final dilution of 1/20k, 1/25k and 1/30k. Freshly prepared conjugate was tested in parallel. Serum #26, 1-29664, 3-29664, A-27239, B-27239, pos pool 030926 and neg pool 030926 were used. HRP conjugated mAb 268:29 lot #030318 was used. 20× conc PBST with 0.042% PVP was used.

PBST with PVP (ELISA 040301)

PBST buffer 20× concentrated was diluted 1/20 and a final concentration of 0.042% PVP was added. This buffer was tested in parallel with PBST tablets (already containing PVP) and 20× conc PBST buffer diluted 1/20. The buffers were used in all steps, i.e. in the sample and conjugate dilution buffer as well as in the washing buffer.

Serum #26, E1, 1-29664, 3-29664, A-27239, B-27239 and gris 13 were used. HRP conjugated mAb 268:29 lot #030318 was used. As conjugate buffer CDS-C with swine serum was used.

4.4. Results

Verification of Prototype

The results show that all 25 previously positive sera also scored positive in the verification batch. Two out of the 25 previously negative sera scored positive.

CDS-C Buffer with Normal Horse Serum

The buffer containing normal horse serum showed similar results as the one with swine sera.

The reading of the lyophilized HRP conjugated mAb decreased at the most 0.4 OD when compared to the freshly prepared conjugate. This drop was noticed in both batches of lyophilized conjugate. It is not affecting the test performance as the calculated PI values corresponded well regardless of obtained OD values.

PBST with PVP

The results show that 20× concentrated PBST solution diluted 1/20 with addition of 0.042% PVP gave similar results as the PBST tablets while 20× conc PBST diluted 1/20 without the PVP showed false negative results.

4.5. Discussion

The verification of the prototype (plate batch 040107) was performed by testing 50 sera previously used when developing the prototype. The verification study showed a 100% agreement with the positive sera while 2 of the 25 negative sera scored positive in the verified batch. The "false" negative results are acceptable as the major importance of this test is to detect positive samples. It has also not been proven that the results from the previous testing are indeed true.

It was found that PBST containing 0.042% PVP showed similar results as using the PBST tablets (that contains PVP). The future kits will therefore contain this buffer. A stability study of the PBST 20× conc with PVP has to be performed to ensure the validity of the kits.

Example 5

5.1 Introduction and Objectives

Detection of serum antibodies against *Lawsonia intracellularis* so far is done by the use of IFA tests (1). These tests rely on an individual and highly subjective judgment in interpretation of results. Recently a sandwich blocking ELISA was developed using highly specific monoclonal antibodies against *L. intracellularis*. The data from this test can be measured and evaluated on an objective basis, which improves reproducibility, repeatability and comparative analyses. In this study first comparative data to the IFA test are presented, demonstrating the suitability and performance of the new test.

5.2 Material and Methods

*L. intracellularis* antigen grown on a McCoy cell culture and captured by a specific monoclonal antibody on microtiter plates was used to detect antibodies against *L. intracellularis* in porcine serum samples. Sera were tested in a 1 to 10 dilution. After 1 h of incubation at 37° C. plates were washed with PBS Tween solution, horseradish-peroxidase labeled monoclonal antibody (different to the capture antibody) was added. The plates were incubated for an additional hour at 37°

C. Unbound antibodies were removed by washing. After incubation with TMB substrate for 10 min at room temperature the reaction was stopped by adding a stop solution. The $OD_{450}$ was read in a photometer for each well. Results were calculated as percent inhibition of controls without serum. 301 field sera, tested in a validated IFA test (2) for antibodies against *L. intracellularis*, were used to evaluate the new ELISA. In addition cross-sectional samples (10 samples each from 9 age groups) from two farms with known Ileitis and one farm with suspected Ileitis were used to demonstrate the diagnostic value of the ELISA in comparison to the IFA.

5.3 Results

Many negative sera resulted in negative inhibition values. Therefore the lowest measured value was set to 0 and all other values were related to this. These data are declared as "relative ELISA values".

Figure 2:
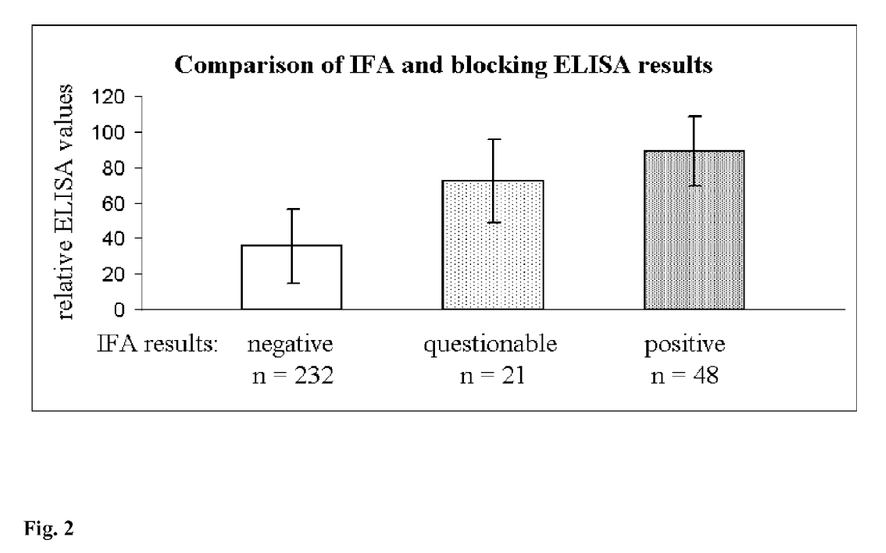
FIG. 2: Results of 301 field sera compared in IFA and ELISA

Results from the 301 field sera are summarized in FIG. 2. The ELISA clearly discriminates between negative (mean relative ELISA value 36) and positive sera (mean relative ELISA value 89). Majority of the samples that scored doubtful in the IFA were positive in the ELISA.

Figure 3:
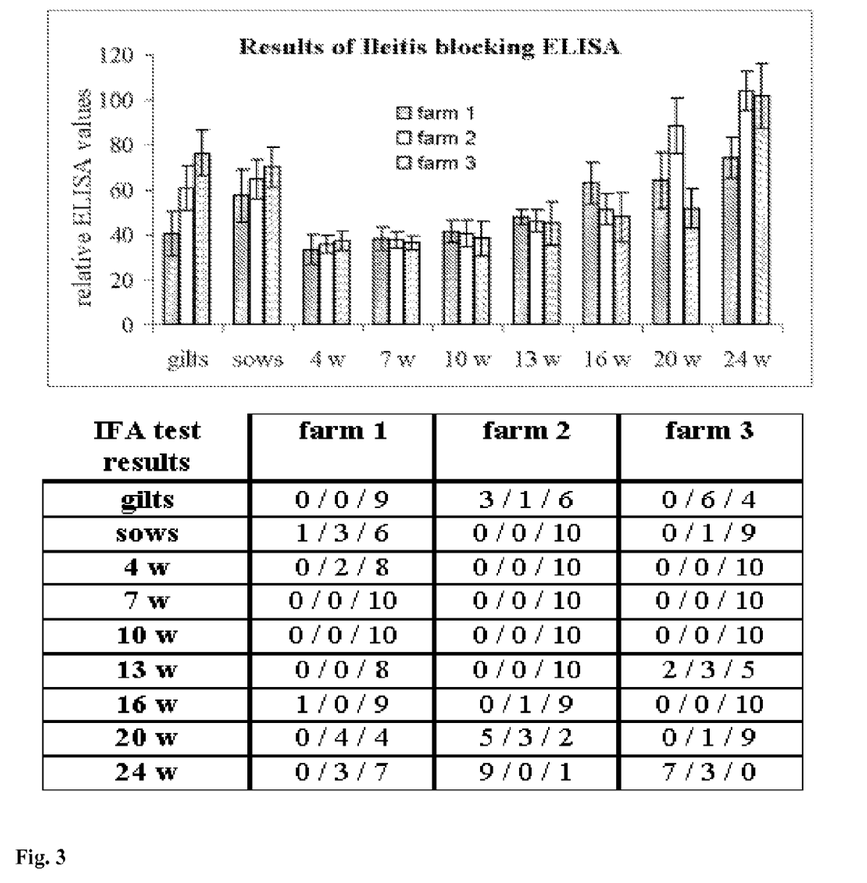
FIG. 3: Results of Ileitis blocking ELISA—cross-sectional screenings in 3 farms

Results from the cross-sectional screenings in the 3 farms are shown in FIG. 3. Both tests clearly detect antibodies against *L. intracellularis* in the 3 farms.

5.4 Discussion

In comparison to the IFA test results the ELISA provides a higher sensitivity. In some groups of the 3 tested farms the result from the ELISA is much more unambiguous than in the IFA test, that gave a lot of questionable results, due to unspecific fluorescence. The serological profiles in the 3 herds corresponded well to previously published data from European herds (3,4). The increase of ELISA values between the group of 10 and 16 weeks old pigs in comparison to the IFA test results indicate, that sera with relative ELISA values greater 55 can be judged as positive.

This new test could help to improve diagnosis of Ileitis in routine samples. The new blocking Ileitis ELISA provides a tool for fast and sensitive screening of large amounts of samples on an objective basis.

REFERENCES

1. Guedes R M C et al., 2002. Can J Vet Res 66:99-107.
2. Knittel J P et al., 1998. AJVR 59:722-726.
3. Biksi I et al., 2002. Proc. 17$^{th}$ IPVS, Ames, Iowa, USA
4. van Aken N et al., 2002. Proc. 17$^{th}$ IPVS, Ames, Iowa, USA.

Example 6

6.1 Introduction and Objectives

Specific diagnosis of Ileitis so far is done by the use of IFA tests for antibody detection (1,2) or PCR (3,4), histological and immuno-staining methods (2,5,6) for antigen detection in feces or intestinal tissue samples. All these methods have specific disadvantages concerning specificity, contamination risk or workload and are not suitable for routine herd screenings on a large scale. So most diagnostic tests are done only for few pigs from a herd. By the use of a recently developed blocking ELISA serological testing becomes easier, more reliable and suitable for herd profiling. Cross-sectional screenings of 22 farms in Germany were performed to demonstrate the diagnostic performance of the new test.

6.2 Material and Methods

Cross-sectional samples from twenty-two German farms were tested in the ELISA. From gilts, sows and pigs 4, 7, 10, 13, 16, 20 and 24 weeks of age samples were taken on each farm (10 samples in each age group). The ELISA was done as described in example 5.

6.3 Results

Figure 4:
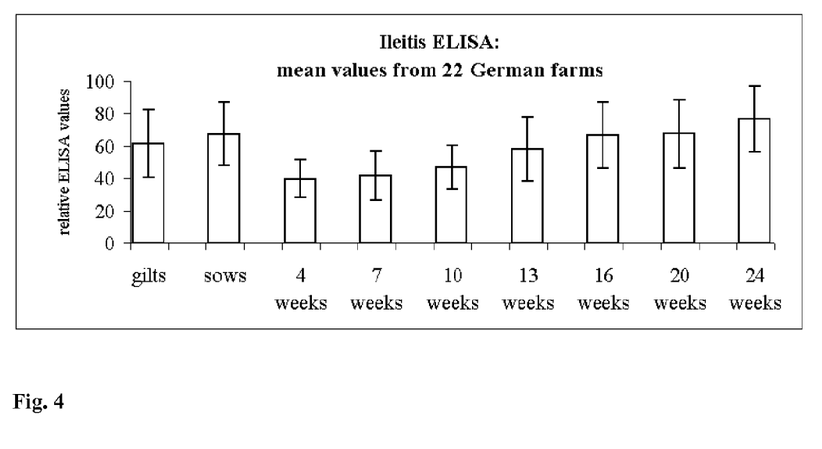
FIG. 4: Results of Ileitis ELISA-22 German farms

In FIG. 4 the mean relative ELISA values from all 22 farms are summarized. Sera from gilts and sows are highly reactive in the ELISA, whereas results from flatdeck piglets of 4 to 10 weeks of age are low. In the fatteners ELISA values increase from 13 to 24 weeks.

Figure 5:
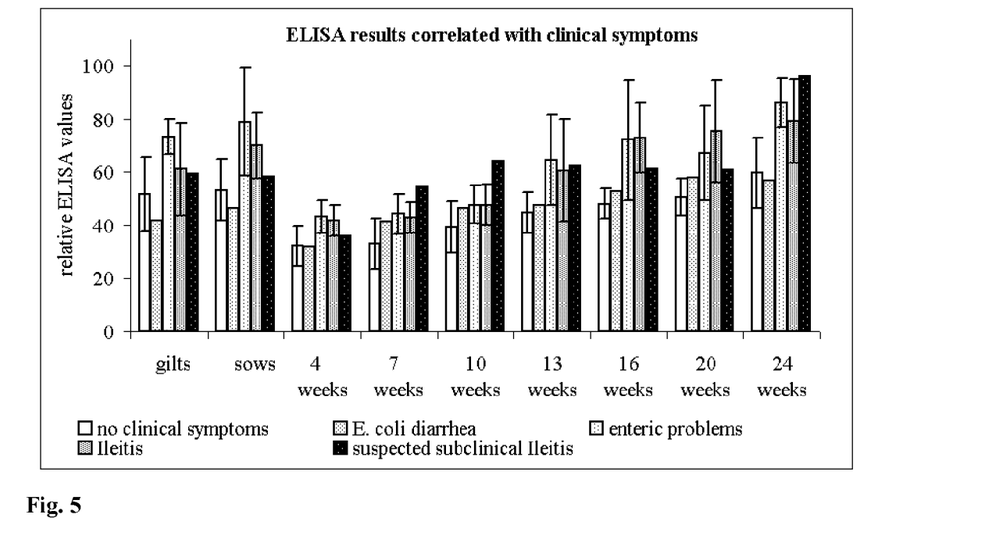
FIG. 5: Correlation of ELISA results with clinical symptoms.

In FIG. 5 mean relative ELISA values are correlated with the clinical symptoms in the farms. The farms No. 5, 6 and 15 had no clinical enteric problems at the time of sampling. In farm No. 3 piglets from 4 to 13 weeks had enteric problems, that were diagnosed as *E. coli* diarrhea. In farm No. 18 prior serological tests indicated the presence of *Lawsonia intracellularis* in the farm without clinical symptoms. In the farms No. 1, 2, 7, 8, 9, 10, 11, 12, 19, 21 and 22 Ileitis was diagnosed before sampling for this study. The farms No. 4, 13, 14, 16 and 20 report enteric problems in growers and fatteners, farms No. 4 and 13 with clinical suspected Ileitis. In farm No. 17 no clinical signs of diarrhea are observed, but antibiotics are used in growers and at the beginning of fattening.

6.4 Discussion

The summarized seroprofile from the 22 farms shows high reactivity in sows and gilts and rising antibody reaction starting at 13 weeks up to 24 weeks. These findings are in agreement with serological data published so far for Ileitis (7,8,9). Pigs from the farms without diarrhea (No. 5, 6, 15 and 18) and the farm with *E. coli* diarrhea (No. 3) showed no significant seroconversion in the ELISA. In the farms with known Ileitis (No. 1, 2, 7, 8, 9, 10, 11, 12, 19, 21 and 22) a clear seroconversion can be detected between week 7 and 13. Interestingly the samples from most of the sow and gilt groups are highly reactive in the ELISA, although most of these pigs have no apparent enteric problems. This might be due to a subclinical infection with *Lawsonia intracellularis*. Results from farm No. 17 seem to indicate a subclinical Ileitis.

The new ELISA according to the invention provides a powerful tool for serological diagnosis of Ileitis suitable for routine testing of large sample sizes and cross-sectional herd screenings.

REFERENCES

1. Knittel J P et al., 1998. AJVR 59:722-726.
2. Guedes R M C et al., 2002. Can J Vet Res 66:99-107.
3. Jones G F et al., 1993. J Clin Microbiol 31: 2611-2615.
4. Suh-D K et al., 2000. J Vet Sci 1:33-37.
5. McOrist S et al., 1989. Vet Pathol 26: 260-264.
6. Huerta B et al., 2003. J Comp Path 129: 179-185.
7. Biksi I et al., 2002. Proc. 17$^{th}$ IPVS, Ames, Iowa, USA
8. van Aken N et al., 2002. Proc. 17$^{th}$ IPVS, Ames, Iowa, USA
9. Holyoake P K et al., 1994. J Clin Microbiol 32: 1980-1985.

What is claimed is:

1. The hybridoma cell line 268:18 deposited at the European Collection and Cell Cultures under the accession number 04092202.

* * * * *